United States Patent
Poland (10) Patent No.: US 11,357,473 B2
(45) Date of Patent: Jun. 14, 2022

(54) PATH TRACKING IN ULTRASOUND SYSTEM FOR DEVICE TRACKING

(71) Applicant: KONINKLIJKE PHILIPS N.V., Eindhoven (NL)

(72) Inventor: Mckee Dunn Poland, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 408 days.

(21) Appl. No.: 16/485,463

(22) PCT Filed: Feb. 5, 2018

(86) PCT No.: PCT/EP2018/052730
§ 371 (c)(1),
(2) Date: Aug. 13, 2019

(87) PCT Pub. No.: WO2018/149671
PCT Pub. Date: Aug. 23, 2018

(65) Prior Publication Data
US 2020/0037983 A1    Feb. 6, 2020

Related U.S. Application Data

(60) Provisional application No. 62/458,789, filed on Feb. 14, 2017.

(51) Int. Cl.
*A61B 8/14* (2006.01)
*A61B 8/08* (2006.01)
(Continued)

(52) U.S. Cl.
CPC .............. *A61B 8/0841* (2013.01); *A61B 8/14* (2013.01); *A61B 8/4254* (2013.01); *A61B 8/463* (2013.01);
(Continued)

(58) Field of Classification Search
CPC ....... A61B 8/0841; A61B 8/14; A61B 8/4254; A61B 8/463; A61B 8/5215;
(Continued)

(56) References Cited

U.S. PATENT DOCUMENTS 8,303,502 B2    11/2012   Washburn et al.
9,282,946 B2     3/2016   Vignon et al.
(Continued)

FOREIGN PATENT DOCUMENTS

WO    2015068073 A1    5/2015

OTHER PUBLICATIONS

International Search Report—PCT/EP2018/052730 dated Feb. 5, 2018.

*Primary Examiner* — Mark D Remaly (57) ABSTRACT

A method for determining a projected track of an object (230) includes measuring movement from frame to frame of a detected object point in a field of view by periodic comparison of positions, extrapolating a locus of periodically detected object points, and qualifying the locus by calculating and applying a threshold to the linearity in a sequence of positions and a threshold to consistency in strength. The method further produces the plurality of ultrasound images by including thereon a rendering of a plurality of lines (310) as a path track indicator (330) on one or more ultrasound images (305) and displaying the projected track of the object when a user moves the tracked object a minimum distance in a region of interest (242) of a subject (240). The method also includes utilizing a motion sensor (234) with a probe (205) to suppress calculation and display of the projected track.

20 Claims, 5 Drawing Sheets

(51) Int. Cl.
 *G06T 7/73* (2017.01)
 *G06T 7/246* (2017.01)
 *A61B 8/00* (2006.01)

(52) U.S. Cl.
 CPC ............ *A61B 8/5215* (2013.01); *G06T 7/248* (2017.01); *G06T 7/74* (2017.01); *G06T 2207/10132* (2013.01); *G06T 2207/30004* (2013.01)

(58) Field of Classification Search
 CPC . G06T 2207/10132; G06T 2207/30004; G06T 2207/30021; G06T 2207/30241; G06T 7/20; G06T 7/248; G06T 7/74; G16H 50/20
 See application file for complete search history.

(56) References Cited

U.S. PATENT DOCUMENTS

| | | |
|---|---|---|
| 2008/0221446 A1 | 9/2008 | Washburn |
| 2009/0124903 A1 | 5/2009 | Osaka |
| 2011/0130641 A1* | 6/2011 | Razzaque .............. A61B 5/067 600/407 |
| 2014/0362114 A1 | 12/2014 | Li et al. |
| 2015/0148664 A1 | 5/2015 | Stolka et al. |
| 2015/0327841 A1 | 11/2015 | Banjanin |
| 2016/0174932 A1 | 6/2016 | Katsuyama |
| 2018/0132944 A1 | 5/2018 | Yan et al. |
| 2018/0279996 A1 | 10/2018 | Cox et al. |

* cited by examiner

PATH TRACKING IN ULTRASOUND SYSTEM FOR DEVICE TRACKING

CROSS-REFERENCE TO PRIOR APPLICATIONS

This application is the U.S. National Phase application under 35 U.S.C. § 371 of International Application No. PCT/EP2018/052730, filed on Feb. 5, 2018, which claims the benefit of U.S. Provisional Patent Application No. 62/458,789 filed on Feb. 14, 2017. These applications are hereby incorporated by reference herein.

BACKGROUND

Technical Field

This disclosure relates to ultrasound devices and more particularly to path tracking in ultrasound systems which have the capability of tracking a device and displaying the position of the device in the ultrasound images.

Description of the Related Art

Precise visualization of objects such as needles or catheters and real-time localization with respect to imaged anatomy are needed for minimally invasive interventions. Intraoperative ultrasound is often used for these purposes. Various ultrasound systems are available in the market which utilize some method for tracking the location of an object in the body of the patient. Such systems share the common attribute that each detected position of the object is digitally represented in the system, allowing display of the positions, and that the positions are updated periodically, typically in conjunction with active scanning, so that the real time ultrasound image display can also show the detected location of the object being tracked. Some systems offer a means of showing the path of the detected object in the image, either as history (where the object came from), or future extrapolation (where it will go if moved in the same direction), or both. Generating such a projected path is typically by means of a method well understood in the art. One method is to include a mechanical fixture like a needle guide mounted on the ultrasound probe which simply constrains the object to follow a predetermined path, i.e., to physically constrain the path of the object with respect to the ultrasound probe as the object is inserted. Other means include locating the device such as by magnetic or electro-magnetic (EM) sensing of the location of the object with respect to similar sensing of the ultrasound probe position.

These systems suffer from complex, expensive parts and circuitry, susceptibility to interference, positional ambiguity due to the deformation of the object (such as bending of the needle), workflow burden such as the obligation to calibrate the positional sensing, etc. There is one system which requires no physical registration of the relative positions of the ultrasound probe (and thus the displayed image) and the object whose position is displayed in the image. U.S. Pat. No. 9,282,946, commonly owned, and incorporated herein in its entirety, describes a system wherein an acoustic signal from the probe is used to activate an acoustic sensor on the tracked object, and via the timing of a returned electrical signal from the object, detect the position of the object with respect to the image itself, thereby obviating all mechanical, magnetic, electromagnetic (EM), or other mechanisms for tracking, and thus also eliminating their cost, complexity, calibration, and susceptibility to error.

In any ultrasound imaging system that also tracks and displays the position of an object, it would be desirable to show the path of the tracked object throughout the ongoing series of displayed images (i.e. through time) without relying upon positioning fixtures or circuitry to detect the relative position of the object with respect to the ultrasound probe. In a system which indeed possesses no such relative registration apparatus, such as the simplified, lower cost system of U.S. Pat. No. 9,282,946, which uses only an acoustic sensor on the object for position detection, showing the path of the detected object presents an unsolved problem. A particular impediment is that while the position of the object is continuously and accurately located in the displayed ultrasound image, the ultrasound probe itself may be rotated or translated with respect to the object, which is largely indistinguishable from motion of the object itself in the medium being scanned.

As further background, a very brief review of ultrasound probes and imaging follows. The versatility of a diagnostic ultrasound system is largely determined by the types of probes which can be used with the system. Linear array transducer probes are generally preferred for abdominal and small parts imaging and phased array transducer probes are preferred for cardiac imaging. Probes may have 1D or 2D array transducers for two dimensional or three dimensional imaging. Indwelling probes are in common use, as are specialty probes such as surgical probes. Each type of probe can operate at a unique frequency range and have a unique aperture and array element count. Some ultrasound systems are designed for grayscale operation or operation at the transmit frequency such as for grayscale and color Doppler imaging while others can additionally perform harmonic imaging. For each of the intended imaging modes, the functional characteristics of the probes, such as physical aperture, transducer element spacing, passband frequencies, etc. determine the requirements for transmitting ultrasound pulses and processing the received echoes. The variation in probe characteristics and functionality means that the processing system operable with a variety of probes must be reprogrammed each time a different probe is put to use.

An example of an object that is tracked during an ultrasound procedure is a needle. During needle biopsy and some interventional therapy, clinicians insert a needle into a subject, such as the body, to reach a target mass. For regional anesthesia, a needle is used to deliver anesthetic to the vicinity of a target nerve bundle in the body, typically in preparation for a surgical procedure. Usually ultrasound imaging is used for live monitoring of the needle insertion procedure. To perform a safe and successful insertion, it is necessary to locate the needle accurately in the guided ultrasound image. Unfortunately, in clinical practice the visibility of the needle itself in the conventional ultrasound image is poor, resulting in difficulty for clinicians to insert the needle accurately. Hence the desirability of a needle tracking system and further, a means of projecting the path of the needle on the image display.

Different techniques have been used to achieve better needle visualization in ultrasound images, for example, adaptively steering the ultrasound beam towards the needle to improve the acoustic reflection of the needle and compounding with the non-steered ultrasound image; manipulating the needle surface coating, geometry and diameter to enhance acoustic reflection; providing an extra optical, magnetic, or electro-magnetic position sensor on the needle to track the needle location in the ultrasound image, etc. In these techniques, either a specially designed needle is used, or an extra position sensor is attached to the needle, or the ultrasound imaging system is manipulated to enhance the visualization of the needle. Those approaches lead to an increase of the cost of providing enhanced needle visualization. In contrast, the simple system mentioned above, which utilizes only an acoustic sensor on the object to provide an electrical signal to the system for location detection, reduces the cost and complexity of the tracking apparatus while increasing its accuracy. But it presents the challenge of how to effectively project the path of the tracked object.

SUMMARY

In accordance with the present principles, an ultrasound probe communicates with an image processor for producing a plurality of ultrasound images by standard methods known in the art, and also provides a method of detecting an object in the ultrasound image field, preferably without the complexity and cost of an apparatus to measure the relative position of probe and object, such as by instead utilizing an acoustic sensor in the object. The system then additionally measures movement from frame to frame of a detected object point in a field of view by periodic comparison of positions, extrapolating a locus of periodically detected object points, and qualifying the locus by calculating and applying a threshold to the linearity in a sequence of positions and a threshold to consistency in strength. The image processor further produces the plurality of ultrasound images by including thereon a rendering of a plurality of lines as a path track indicator on one or more ultrasound images of the plurality of ultrasound images, displaying the projected track of the object when a user moves the tracked object a minimum distance in a region of interest of a subject, and utilizing a motion sensor in the ultrasound probe or motion detection from image data to suppress calculation and display of the projected track when the ultrasound probe is rotating or translating in space.

A system includes an ultrasound probe and an image processor for producing a plurality of ultrasound images by including a pair of reference lines passing as parallel tangents on opposite sides of a location circle displayed by the system to locate an object, displaying a projected track of the object as the tracked object moves within a region of interest of a subject, and utilizing a motion sensor to suppress calculation and display of the projected track when the ultrasound probe is rotating or translating in space.

A method for determining a projected track of an object includes measuring movement from frame to frame of a detected object point in a field of view by periodic comparison of positions, extrapolating a locus of periodically detected object points, and qualifying the locus by calculating and applying a threshold to the linearity in a sequence of positions and a threshold to consistency in strength. The method further includes rendering a plurality of lines as a path track indicator on an ultrasound image and displaying the projected track of the object when a user moves the tracked object a minimum distance in a region of interest of a subject. The method also includes utilizing a motion sensor in an ultrasound probe or motion detection from image data to suppress calculation and display of the projected track when the ultrasound probe is rotating or translating in space.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

In accordance with the present principles, systems, devices and methods are provided to track and display a projected track of an object. The present principles provide embodiments where the systems, devices and methods are self-referential in that they do not rely on an external positioning system to determine the validity of the detected path.

In one useful embodiment, an ultrasound system includes an object location apparatus where the object location apparatus utilizes the ultrasound acoustic pulses generated by the ultrasound system to energize the tracking sensor and a method of automatically determining and displaying the projected track of the object in the scanned medium. The method comprises a) measuring movement from frame to frame of the detected object point in the field of view by periodic comparison of positions, b) extrapolating the locus of periodically detected points, c) qualifying the locus by calculating and applying a threshold to the linearity in the sequence of positions and a threshold to consistency in strength, d) rendering a plurality of lines or another path track indicator on the ultrasound image as an overlay, e) using data from the previous steps for displaying the projected track when the user moves the tracked object a minimum distance in the medium, and f) utilizing a motion sensor in the ultrasound probe or motion detection from the image data to suppress calculation and display of the track projection when the ultrasound probe is rotating or translating in space.

It should be understood that the present invention will be described in terms of medical instruments; however, the teachings of the present invention are much broader and are applicable to any acoustic instruments. In some embodiments, the present principles are employed in tracking or analyzing complex biological or mechanical systems. In particular, the present principles are applicable to internal and/or external tracking procedures of biological systems and procedures in all areas of the body such as the lungs, gastro-intestinal tract, excretory organs, blood vessels, etc. The functional elements depicted in the FIGS. may be implemented in various combinations of hardware and software and provide functions which may be combined in a single element or multiple functional elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

It will also be understood that when an element such as a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Figure 1:
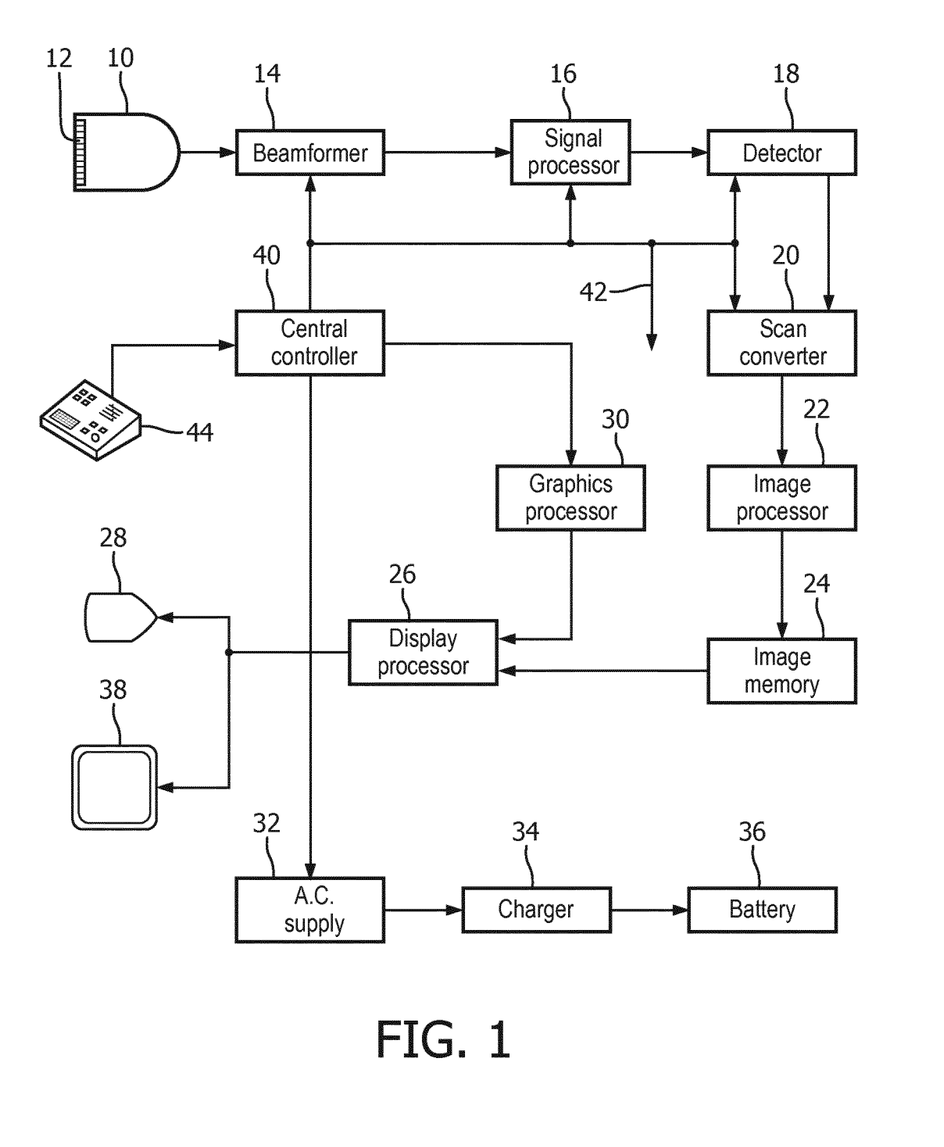
FIG. 1 is a block/flow diagram showing an ultrasonic diagnostic imaging system, in accordance with one embodiment.

Referring now to the drawings in which like numerals represent the same or similar elements and initially to FIG. 1, an ultrasonic diagnostic imaging system is illustratively shown in accordance with one embodiment.

Referring first to FIG. 1, an ultrasonic diagnostic imaging system showing one embodiment of the present invention is shown in block diagram form. An ultrasound probe 10 transmits and receives ultrasound waves from the piezoelectric elements of an array of transducer elements 12. For imaging a planar region of the body a one-dimensional (1-D) array of elements may be used, and for imaging a volumetric region of the body a two-dimensional (2-D) array of elements may be used to steer and focus ultrasound beams over the image region. A transmit beamformer actuates elements of the array to transmit ultrasound waves into the subject. The signals produced in response to the reception of ultrasound waves are coupled to a receive beamformer 14. The beamformer 14 delays and combines the signals from the individual transducer elements to form coherent beamformed echo signals. When the probe includes a 2-D array for 3D imaging, it may also include a microbeamformer which does partial beamforming in the probe by combining signals from a related group ("patch") of transducer elements as described in U.S. Pat. No. 6,709,394. In that case the microbeamformed signals are coupled to the main beamformer 14 in the system which completes the beamforming process.

The beamformed echo signals are coupled to a signal processor 16 which processes the signals in accordance with the information desired. The signals may be filtered, for instance, and/or harmonic signals may be separated out for processing. The processed signals are coupled to a detector 18 which detects the information of interest. For B mode imaging amplitude detection is usually employed, whereas for spectral and color Doppler imaging the Doppler shift or frequency can be detected. The detected signals are coupled to a scan converter 20 where the signals are coordinated to the desired display format, generally in a Cartesian coordinate system. Common display formats used are sector, rectilinear, and parallelogram display formats. The scan converted signals are coupled to an image processor for further desired enhancement such as persistence processing. The scan converter may be bypassed for some image processing. For example the scan converter may be bypassed when 3D image data is volume rendered by the image processor by direct operation on a 3D data set. The resulting two dimensional or three dimensional image is stored temporarily in an image memory 24, from which it is coupled to a display processor 26. The display processor 26 produces the necessary drive signals to display the image on a docking station image display 28 or the flat panel display 38 of the portable system. The display processor also overlays the ultrasound image with graphical information from a graphics processor 30 such as system configuration and operating information, patient identification data, and the time and date of the acquisition of the image.

A central controller 40 responds to user input from the user interface and coordinates the operation of the various parts of the ultrasound system, as indicted by the arrows drawn from the central controller to the beamformer 14, the signal processor 16, the detector 18, and the scan converter 20, and the arrow 42 indicating connections to the other parts of the system. The user control panel 44 is shown coupled to the central controller 40 by which the operator enters commands and settings for response by the central controller 40. The central controller 40 is also coupled to an a.c. power supply 32 to cause the a.c. supply to power a battery charger 34 which charges the battery 36 of the portable ultrasound system when the portable system is docked in the docking station.

It is thus seen that, in this embodiment, the partitioning of the components of FIG. 1 is as follows. The central controller 40, beamformer 14, signal processor 16, detector 18, scan converter 20, image processor 22, image memory 24, display processor 26, graphics processor 30, flat panel display 38, and battery 36 reside in the portable ultrasound system. The control panel 44, display 28, a.c. supply 32 and charger 34 reside on the docking station. In other embodiments the partitioning of these subsystems may be done in other ways as design objectives dictate.

Figure 2:
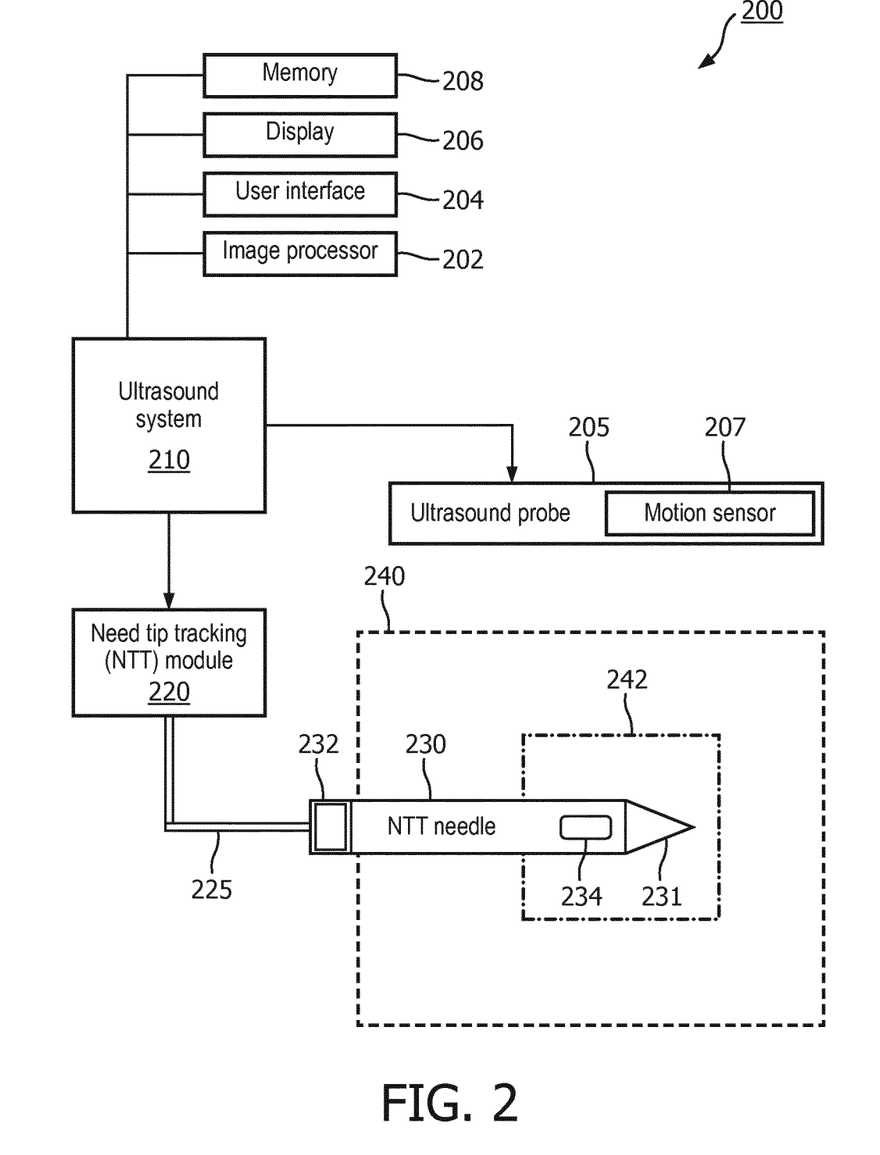
FIG. 2 is a diagram showing a needle tip tracking (NIT) system in communication with an ultrasound system, in accordance with one embodiment.

Referring to FIG. 2, a diagram showing a needle tip tracking (NTT) system in communication with an ultrasound system is presented in accordance with one embodiment.

The tracking system 200 includes an ultrasound system 210 in communication with a needle tip tracking (NTT) module 220. The NTT module 220 is connected to an object, such as an NTT needle 230 via NTT cable 225. The ultrasound system 210 may include an image processor 202, a user interface 204, a display 206, and a memory 208. Additionally, an ultrasound probe 205 may be connected to the ultrasound system 210. The ultrasound probe 205 may be positioned adjacent the subject 240. The subject 240 can be, e.g., a patient. The ultrasound probe may include a motion sensor 207. The motion sensor 207 of the probe 205 detects motion of the probe 205 with respect to the tissue of the subject 240.

The NTT needle 230 is inserted into a volume or region of interest 242 of the subject 240. The needle 230 is tracked ideally from the point of entry at the skin surface all the way to the point where it stops insertion. For regional anesthesia, for instance, the stopping point is near a visualized nerve bundle, at which point the anesthetic is injected through the needle cannula so that it optimally bathes the nerve bundle.

The distal end of the NTT needle 230 may include an ultrasound sensor 234, whereas the proximal end of the NTT needle 230 may include a hub 232. The distal end of the NTT needle may be, e.g., a pointed end or beveled tip 231. Of course, one skilled in the art may contemplate a number of different design configurations for the distal end of the NTT needle 230. U.S. Pat. No. 9,282,946, commonly owned, and incorporated herein in its entirety, provides further information regarding the tracking system 200 and various beamforming techniques.

Figure 3:
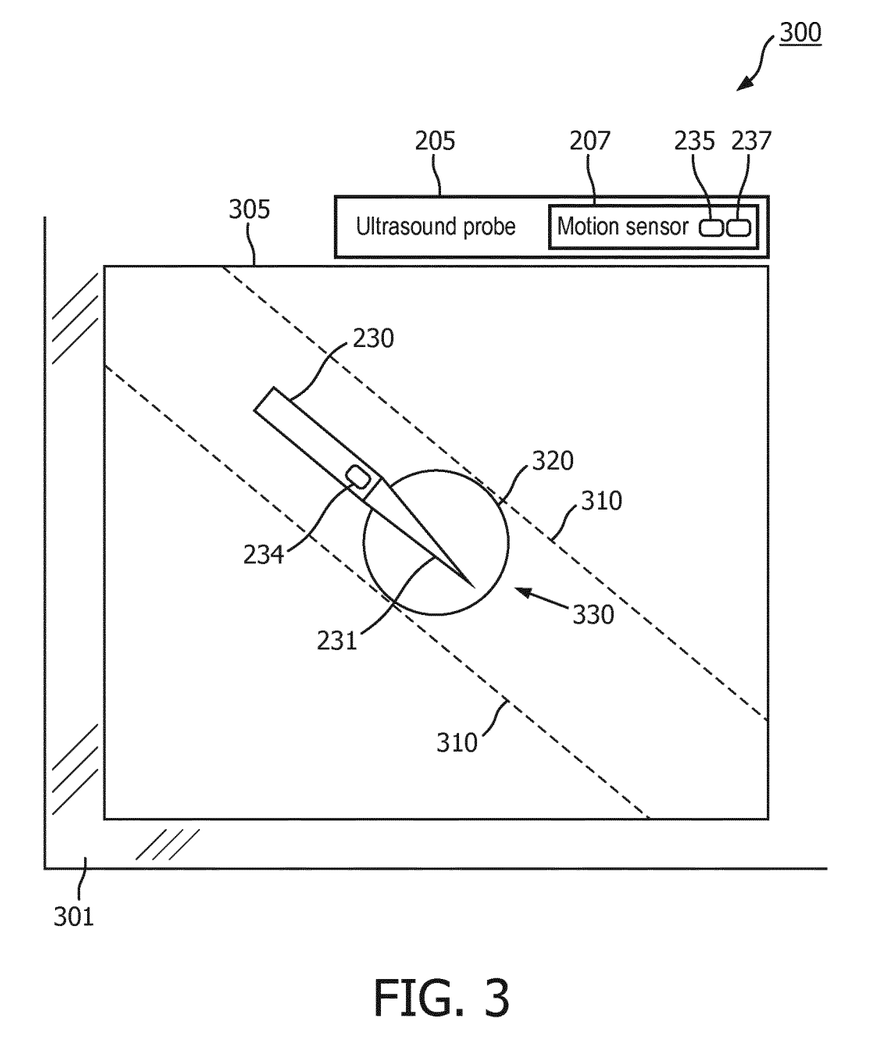
FIG. 3 is a diagram showing an ultrasound image depicting a pair of reference lines passing as parallel tangents on opposite sides of a location circle displayed by the system in response to the position of the object/needle, in accordance with one embodiment.

Referring to FIG. 3, a diagram showing an ultrasound image depicting a pair of reference lines passing as parallel tangents on opposite sides of a location circle displayed by the system in response to the position of the object/needle is presented in accordance with one embodiment.

The diagram illustrates an ultrasound image 305. The ultrasound image 305 is shown on a screen 300 of a display device 301. The ultrasound image 305 depicts the NTT needle 230 travelling along a tracked path 330 defined by a pair of parallel lines 310. The pair of parallel lines 310 engage opposed endpoints of a location circle 320. The distal end of the NTT needle 230 includes a pointed end or beveled tip 231. The distal end of the NTT needle 230 further includes an ultrasound sensor 234. Sensor 234 may comprise, in one embodiment, a single piezo electric transducer element. A fine cable connection from sensor 234 is integrated into the NTT needle 230 and connects to NTT module 220. The ultrasound probe 205 includes the motion sensor 207, which can include an accelerometer 235 and a gyroscope 237 to continuously monitor movement of the ultrasound probe 205.

FIGS. 2 and 3 will be discussed in tandem. In the needle tracking system that accompanies the ultrasound scanning system, the path tracking feature automatically displays a pair of reference lines 310 passing as parallel tangents on opposite sides of the location circle 320 displayed at the needle tip 231. The lines 310 project in the direction of the last motion of the location circle 320 and also in the reverse direction. When the needle tip 231 is motionless for a predetermined period, path tracking disappears (i.e., is not displayed on the display screen 300).

As the physician inserts or withdraws the needle 230, the pair of lines 310 appear or are displayed, thus forming a constructed, virtual lane 330 in which the needle 230 is moving, that is, a linear region, a straight path, in which the needle shaft and tip 231 proceed to move if insertion or withdrawal continues. The path 330 is shown when the needle tip location locus meets certain conditions, such as minimum strength and stability of the tracking signal, movement over a minimum distance in a minimally co-linear series of sample positions, etc. The path lines 310 extend to the boundaries of the image 305, and may be solid, dotted, colored, etc. to indicate status, such as confidence based on tracking signal strength.

Further, the motion sensor 207, which includes both accelerometer and gyroscope components 235, 237, is used to continuously monitor movement of the probe 205, and to suppress display of the path lines 310 if the probe 205 is in motion, since such movement results in changes to the tracked needle position on the displayed image, independent of any actual insertion or withdrawal of the needle. In general, detecting probe motion causes immediate suppression of the lane lines 310, whereas mere lack of needle insertion/withdrawal results in lane display suppression after a number of seconds. Thus, the physician may effectively invoke the display of the tracked path of the instrument/needle 230 by holding the ultrasound probe 205 steady and moving the needle 230, per the typical workflow, yet may also pause for some seconds to study the projected path lane 330 while not moving the needle 230. Translation of the probe 205 in any axis is detected as a change in total force, equivalent to a change in acceleration, such that the magnitude of the 3-dimensional force vector deviates from 1.0 g, the baseline gravity vector. Rotation in any axis is detected as non-zero angular velocity, but rotation in the X axis ignored, since that corresponds to elevation tilt of the ultrasound probe 205, which by itself does not necessarily diminish the needle tip display nor invalidate the displayed path 330. Instead, the above mentioned constraint on needle tracking signal strength serves to suppress the path display as soon as pure X rotation effectively moves the needle tip 231 out of the rendered image plane.

Therefore, FIGS. 2 and 3 provide a novel way of both locating and tracking the tip 231 of needle 230. The ultrasound system 210, in conjunction with probe 205, actuate a series of acoustic transmissions that generate 2D sweeps of scan lines or scan beams. The acoustic echo data gathered from the sweeps is detected, scan converted, and rendered as image frames on a system display as described above. Additionally, in each sweep, the acoustic transmit beams insonicate the sensor 234 on tip 231 of needle 230. The scan line with the transmit beam that is closest to the sensor 234 produces the return signal from that sensor with the highest amplitude of the sweep. Further, the depth of the sensor 234, and therefore the tip 231, is determined from the acoustic time of flight of the transmit pulse from the probe 205 transmission surface to the sensor 234, as indicated by the time of the return electrical signal with respect to the time of the start of transmission at the probe in any given scan line. In this way, the system detects the location of the needle tip as a point in the 2D sweep of scan lines, with both sweep line position coordinate and line depth coordinate. Utilizing standard scan conversion geometry, those two coordinates are transformed into the standard Cartesian X, Y coordinates used in rendering a point. In this embodiment, the coordinates are used as a center of a rendered circle indicating the position of the needle tip. The circle has a small radius to represent the uncertainty arising from variations in acoustic time of flight through the tissue, from resolution limits of the scan timing, etc. The needle tip is thus represented as lying somewhere within the rendered circle on the displayed image on which the circle is overlaid, frame by frame. Over a continuous series of scan sweeps, which create a series of displayed image frames, the series of object points are thus detected, rendered as circles on the image frames, recorded, and analyzed for sufficiently accurate needle location detection. If the needle does not move, the path lines or lane is suppressed (i.e., not illustrated/depicted), whereas if the needle moves, a path track is displayed.

To calculate the path track, a common linear regression may be utilized on a series of the stored object points as X, Y coordinates. For a series of N object points, the standard linear regression formula is shown below, yielding the equation for the line of the path track in the same coordinate system. Rendering the path track on the ultrasound image 305 is preferably represented by lines 310 surrounding virtual lane 330, where the line equation as calculated in the regression is further offset in a direction orthogonal to its slope by a distance equal to the radius of the rendered object circle, in both positive and negative directions.

linear regression form $y=m \cdot x+b$ for N value pairs of $X_i, Y_i$ slope $m=(N\Sigma_i(X_iY_i)-\Sigma_i(X_i)\Sigma_i(Y_i)/(N\Sigma_i(X_i^2)-\Sigma_i(X_i)^2)$ intercept $b=(\Sigma_i(Y_i)-m\Sigma_i(X_i))/N$ Besides the aforementioned motion sensor 207 in probe 205, an alternative method of detecting probe motion is to detect relative movement between image data and the ultrasound probe on a frame by frame basis. The technique performs simple image correlation to detect gross probe motion when the ultrasound probe is coupled to the body, and can thereby suppress the display of the tracked path until the ultrasound probe is once again steady and the needle track has been re-established. Standard methods of correlation of image data between successive frames, optimally taken from a region of the image near the probe face, can be used to generate an average correlation of the whole frame, which is then compared to a threshold that represents substantial image motion. If above the threshold, image motion is asserted, and display of the tracked path is suppressed.

Figure 4:
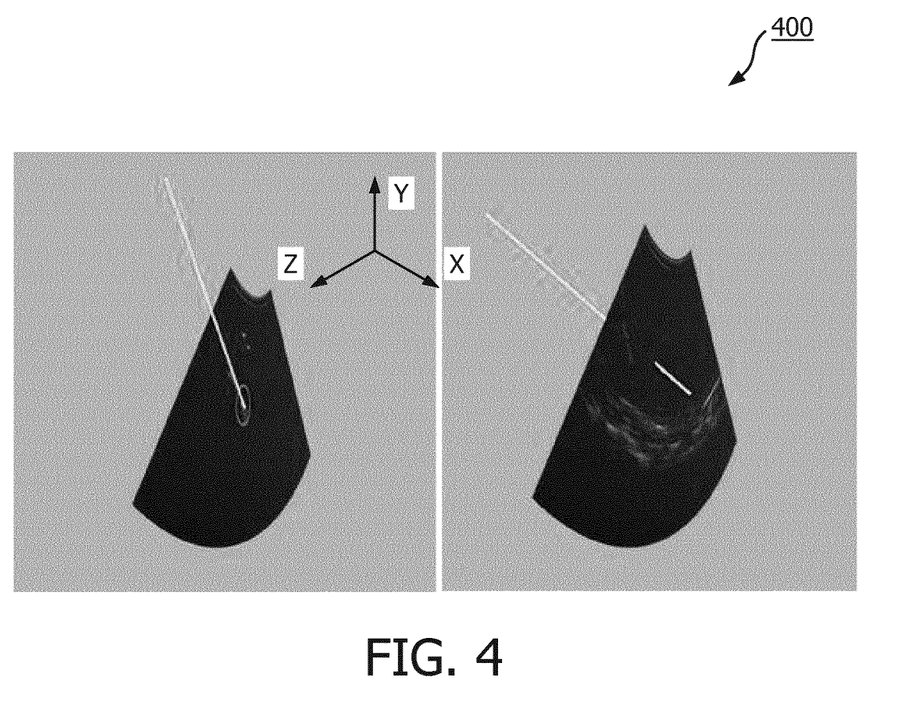
FIG. 4 is a diagram showing a needle inserted into a patient with the ultrasound probe scanning it "in-plane" or "transverse," in accordance with one embodiment.

FIG. 4 is a diagram 400 showing a needle inserted into a patient with the ultrasound probe scanning it "in-plane" or "transverse," in accordance with one embodiment.

In practice, a needle 230 may be inserted into a patient 240 with the ultrasound probe 205 scanning it "in-plane" or "transverse/out-of-plane." The left-hand side illustration shows "in-plane" scanning, whereas the right-hand side illustration shows "out-of-plane" or "transverse" scanning. When scanning in-plane, the majority of the needle shaft is typically visualized (though frequently poorly, as mentioned previously), and insertion of the needle produces a natural projection of the path 330 of the needle shaft in the plane where the tip may continue to appear but is in any case tracked. In the transverse scanning position, the path 330 is mostly axial with respect to the probe face, and, thus, has a different interpretation. While still representing the path of the needle tip 231, it is effectively showing the projection of the path 330 on the image plane as the tip 231 of the needle 230 moves from behind the plane to the front of the plane, or in the reverse direction. In this case, moderate rotation of the probe 205 in the X axis results in generation of sufficient needle tip locus points to display the projected vertical path. Rotation to the point where the needle tip signal is lost results in suppression of the path lines 310, as is appropriate. Therefore, in summary, there is no change to the path tracking algorithm for these two cases. Indeed, the system is unaware of which type of scan is chosen by the physician and the algorithm behaves in the same manner for each scan.

Finally, the path tracking algorithm affords the needle tracking system an improvement in tracking reliability in that spurious needle tip locations, which are sometimes generated in the presence of simultaneous ultrasound pulse reverberation and acoustic shadowing, may be beneficially rejected if the falsely detected locations are outside of the previously detected path. Since the spurious detections are almost always transient, the detected path can be used as boundaries for needle tip location as long as the path is valid. Therefore, the path tracking feature serves to enhance the reliability of the needle tracking system, as well as add utility for procedure visualization.

Figure 5:
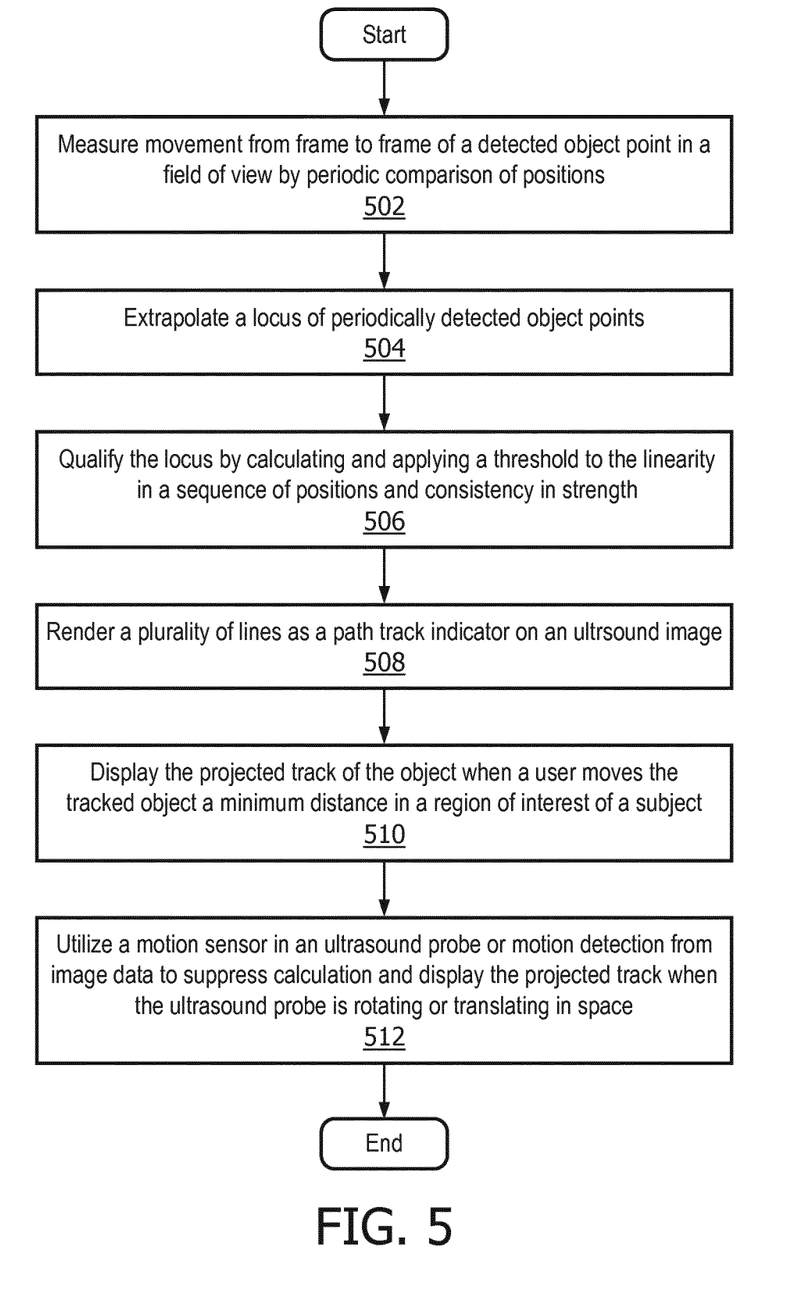
FIG. 5 is a flow diagram showing a method for determining and displaying a projected track of an object/needle within a region of interest of an object, in accordance with illustrative embodiments.

Referring to FIG. 5, a flow diagram showing a method for determining and displaying a projected track of an object/needle within a volume or region of interest of an object is illustrated.

In block 502, measure movement from frame to frame of a detected object point in a field of view by periodic comparison of positions.

In block 504, extrapolate a locus of periodically detected object points.

In block 506, qualify the locus by calculating and applying a threshold to the linearity in a sequence of positions and a threshold to consistency in strength.

In block 508, render a plurality of lines as a path track indicator on an ultrasound image.

In block 510, display the projected track of the object when a user moves the tracked object a minimum distance in a region of interest of a subject.

In block 512, utilize a motion sensor in an ultrasound probe or motion detection from image data to suppress calculation and display the projected track when the ultrasound probe is rotating or translating in space.

In summary, in an ultrasound system which includes an object location apparatus, wherein the object location apparatus utilizes the ultrasound acoustic pulses generated by the ultrasound system to energize the tracking sensor, a method of automatically determining and displaying the projected track of the object in the scanned medium is introduced. The method is self-referential in that it does not rely on an external positioning system to determine the validity of the detected path. Specifically, the exemplary tracking system of certain embodiments of the present invention requires no fixed positional reference point for the object/needle. Instead, using the needle tracking system to get the needle tip position in the imaging field, the tracking system operates self-referentially in that it relies on the locus of sequential positions detected within the imaging field in order to display a plausible path, or suppress such a display if the locus is excessively non-linear or if the probe moves. The probe's motion sensor may be utilized for detection of probe movement only. In a preferred embodiment, the novel aspects include at least a) extrapolation of un-referenced needle tip locations and/or b) qualification for the purpose of suppression of path display via conditions such as co-linearity, signal strength, and probe movement, the latter being detected at least by the probe's motion sensor or by image data correlation. Therefore, the solution provided by the tracking system of the present invention is differential location from one detected point to the next, with extrapolation and display qualification using measurements of the detection signals, using path linearity, and using probe movement.

In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for calculation and display of a projected path track of object points in an ultrasound image (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. An ultrasound system comprising:
an ultrasound probe configured to produce acoustic transmissions and receive acoustic echo data in response to the acoustic transmissions;
an image processor coupled to the ultrasound probe, the image processor configured to:
produce a plurality of ultrasound images based on the acoustic echo data,
produce a projected track of an object by:
detecting an object point of the object in a field of view of the ultrasound probe,
measuring movement from frame to frame of the detected object point in the field of view by periodic comparison of positions of the object in the plurality of ultrasound images, and
extrapolating a locus of object points of the object based on the measured movement, and
provide, on the plurality of ultrasound images, a rendering of a plurality of lines as a path track indicator, wherein the plurality of lines comprises a pair of reference lines separate from the object and positioned on opposite sides of the object to indicate the projected track of the object, and
suppress calculation and display of the projected track of the object when the ultrasound probe rotates or translates in space; and
a display coupled to the image processor, the display configured to display the plurality of ultrasound images including the projected track of the object when a user moves the object a minimum distance in a region of interest of a subject.

2. The system as recited in claim 1, further comprising a motion sensor in the ultrasound probe to detect a motion of the ultrasound probe.

3. The system as recited in claim 2, wherein the motion sensor includes an accelerometer and a gyroscope to continuously monitor movement of the ultrasound probe.

4. The system as recited in claim 3, wherein the image processor is configured to detect the motion of the ultrasound probe based on detection of relative movement between image data and the ultrasound probe on a frame by frame basis.

5. The system as recited in claim 1, wherein the image processor is further configured to detect a motion of the ultrasound probe and compare data from the plurality of ultrasound images.

6. The system as recited in claim 1, wherein the image processor is further configured to render a location circle to locate the object in the plurality of ultrasound images and render the pair of reference lines pa as parallel tangents on opposite sides of the location circle.

7. The system as recited in claim 6, wherein the image processor is configured to render the pair of reference lines projected in a direction of a last motion of the location circle.

8. The system as recited in claim 6, wherein the image processor is configured to render the pair of reference lines to form a virtual lane that extends up to a boundary of one or more images of the plurality of ultrasound images.

9. The system as recited in claim 6, wherein the display is configured to display the pair of reference lines when the ultrasound probe is motionless and the object is in motion.

10. The system as recited in claim 6, wherein, when the object is motionless, the display is configured to display the pair of reference lines for a predetermined period of time for observation by the user.

11. The system as recited in claim 1, wherein the image processor is configured to enable in-plane scanning or transverse scanning of the object by the ultrasound probe.

12. The system as recited in claim 1, wherein the image processor is configured to discard subsequent object points detected outside a previously produced projected track.

13. A method for determining a projected track of an object, the method comprising:
   detecting an object point of the object in a field of view of an ultrasound probe;
   measuring movement from frame to frame of the detected object point in the field of view by periodic comparison of positions of the object in a plurality of ultrasound images;
   extrapolating a locus of object points of the object based on the measured movement to produce a projected track of the object;
   qualifying the locus by calculating and applying a threshold to a linearity in a sequence of positions and a threshold to consistency in strength of the detected object point;
   rendering a plurality of lines comprising a pair of reference lines separate from the object and positioned on opposite sides of the object as a path track indicator on one or more of the plurality of ultrasound images;
   displaying the plurality of ultrasound images including the projected track of the object when a user moves the object a minimum distance in a region of interest of a subject; and
   utilizing a motion sensor with an ultrasound probe or motion detection from image data to suppress calculation and display of the projected track of the object when the ultrasound probe is rotating or translating in space.

14. The method as recited in claim 13, wherein the pair of reference lines pass as parallel tangents on opposite sides of a location circle displayed to locate the object.

15. The method as recited in claim 14, wherein the pair of reference lines project in a direction of a last motion of the location circle.

16. The method as recited in claim 14, wherein the pair of reference lines form a virtual lane that extends up to a boundary of the one or more images of the plurality of ultrasound images displayed on a display screen.

17. The method as recited in claim 14, wherein the pair of reference lines are visible when the ultrasound probe is motionless and the object is in motion.

18. The method as recited in claim 14, wherein, when the object is motionless, the pair of reference lines are visible for a predetermined period of time for observation by the user.

19. The method as recited in claim 13, wherein the user scans the object by the ultrasound probe by in-plane scanning or transverse scanning methodologies.

20. The method as recited in claim 13, wherein subsequent object points detected outside a previously detected projected track are discarded.

\* \* \* \* \*